United States Patent [19]

Severn et al.

[11] Patent Number: 5,015,586

[45] Date of Patent: May 14, 1991

[54] METHOD AND APPARATUS USEFUL IN GEOCHEMICAL EXPLORATION FOR PETROLEUM OILS

[75] Inventors: Shawn R. T. Severn, Victoria; Henry Rodriguez, Sidney; Renato R. A. Danesin; Bryan E. Imber, both of Victoria, all of Canada

[73] Assignee: Banbury Gold Mines Ltd., Vancouver, Canada

[21] Appl. No.: 436,335

[22] Filed: Nov. 13, 1989

[51] Int. Cl.⁵ ............................................. G01N 33/24
[52] U.S. Cl. ........................................ 436/29; 422/61; 435/9; 435/810; 436/30; 436/31
[58] Field of Search ................... 422/61; 436/29, 30, 436/31; 435/9, 810

[56] References Cited

U.S. PATENT DOCUMENTS 4,612,281 9/1986 Desmonts et al. .............. 436/519 X

Primary Examiner—Robert J. Warden
Assistant Examiner—Jill Johnston
Attorney, Agent, or Firm—Christensen, O'Connor, Johnson & Kindness

[57] ABSTRACT

Method and kit useful in geochemical exploration for petroleum oils. The method involves contacting a soil sample with serum from a rabbit that has not been immunized with petroleum oils, and determining the amount of the bound serum as indicative of the presence of petroleum oils in the geographic region from which the sample was obtained.

1 Claim, 4 Drawing Sheets

METHOD AND APPARATUS USEFUL IN GEOCHEMICAL EXPLORATION FOR PETROLEUM OILS

TECHNICAL FIELD

The invention relates to geochemical exploration for petroleum oils.

BACKGROUND OF THE INVENTION

The search for new oil and gas resources and the expansion of the current resource base is an ongoing and expensive procedure. In 1988 the oil and gas industry in the United States spent over $12,000,000,000 on exploration. Since the oil crisis of the late 1970s, the industry has actively tried to expand and develop new resources as well as extend the life of its current resources. New oil exploration and the expansion of current resources is a time-consuming process. Like most exploration industries the oil and gas industry has reached an advanced level of sophistication; however, it still relies heavily on luck and determination to extend its wealth. New, routine, and inexpensive procedures that enhance the probability of finding new reserves are very attractive to the industry. Especially attractive are procedures that have the potential for use during the field component of the exploration cycle.

The oil and gas industry relies heavily on a combination of physical, geological, and chemical methods for exploration. Current chemical analytical procedures require specialized equipment and a high level of technical competence. There is typically a considerable delay between acquiring a sample and the completion of an analysis. Furthermore, due to the often trace amounts of oil in the samples, significant quantities of sample are required, e.g., 50–100 grams.

The industry has collected a large reservoir of sediment samples during the past twenty years of exploration. It would be advantageous for the industry to reevaluate these samples for an indication of the presence of exploitable petroleum deposits. The resulting data may allow an oil company to significantly expand its current resources or find new resources without having to reenter the field cycle for further collection. This form of exploration is extremely cost-effective and could contribute significantly to the expansion of the industry's reserves.

There are also a series of developments exploring the use of so-called "biodegrading bacteria" as a way to explore for oil in sediments. Two approaches are used here. One involves the development of specific probes to detect quantities of bacteria in the soil samples. These can be further subdivided into immunological and DNA-based procedures. In both cases the procedure relies on the detection of a unique characteristic of the bacteria of interest. The underlying assumption is that the presence of the bacteria or its unique biochemical component is directly or indirectly related to the presence of oil in the soil or sediment which corresponds to an underlying oil formation. The second approach involves analyzing soil samples for their potential biodegradability. This involves the use of known biodegrading bacteria which are inoculated into the soil samples. The amount of growth of the bacteria or production of some byproduct of degradation, such as $CO_2$, is then used to evaluate the amount of oil available. The advantage of these methods is that they tend to be very sensitive and can be performed relatively quickly. However, they have not gained wide acceptance in the industry, primarily because performing direct measurements of oil in soil when possible is more direct and is currently easier to interpret.

Accordingly, there is a continuing need for new methods for facilitating a determination of the presence of petroleum deposits. There is also a need for simple and economical methods of determining the presence of hydrocarbons and other organic chemicals in samples.

SUMMARY OF THE INVENTION

The invention provides methods and kits for conveniently and economically detecting petroleum oils in soil samples. The method is based on the serendipitous observation that sera from both immunized and unimmunized rabbits are capable of an immunologically nonspecific interaction with petroleum hydrocarbons in soil samples.

DETAILED DESCRIPTION OF THE PREFERRED EMBODIMENTS

Figure 1:
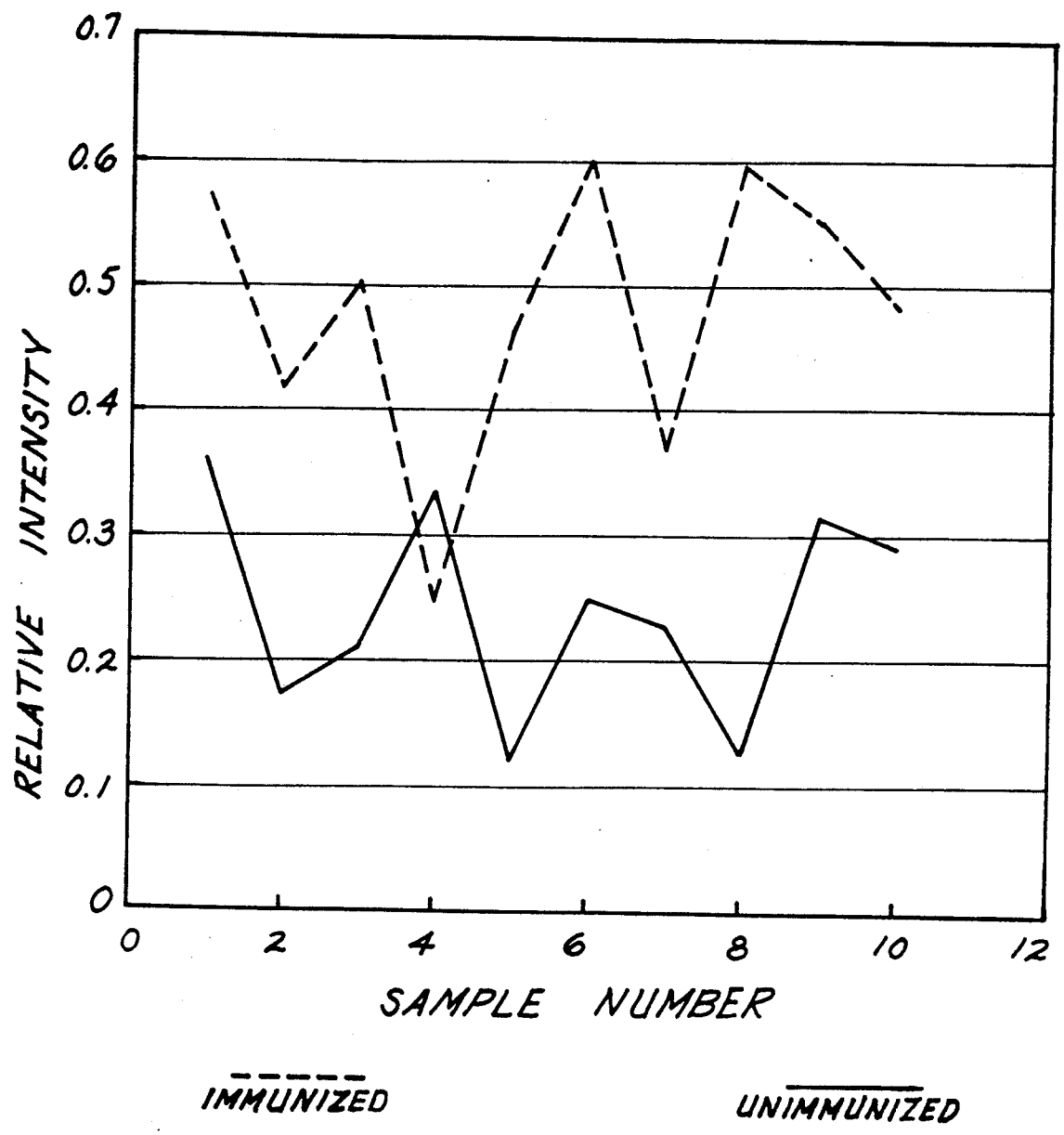
FIGS. 1 and 2 are graphs showing rabbit serum binding in soil without and with hydrocarbons, respectively, as described in EXAMPLE 1.
Figure 2:
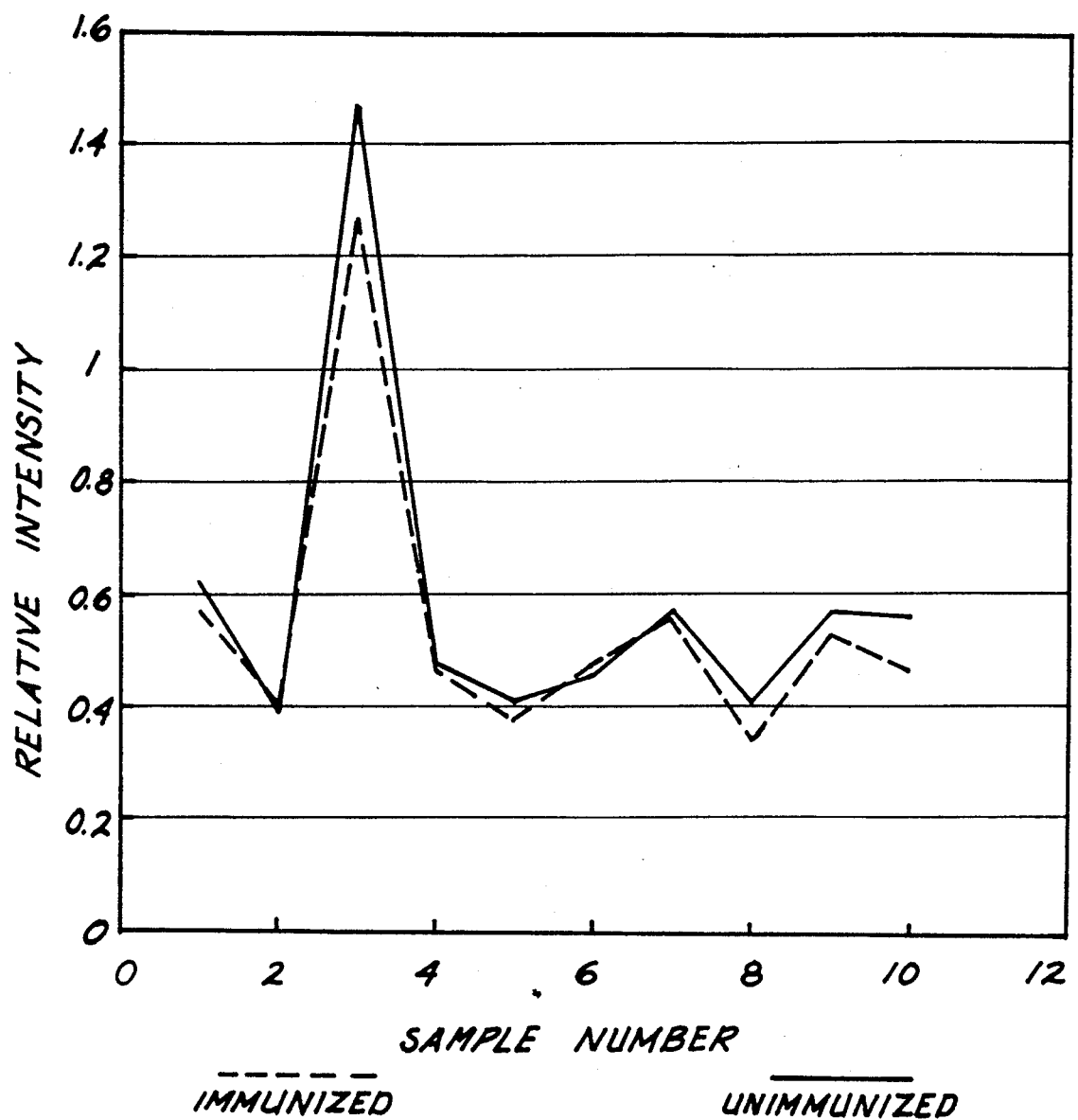
Figure 3:
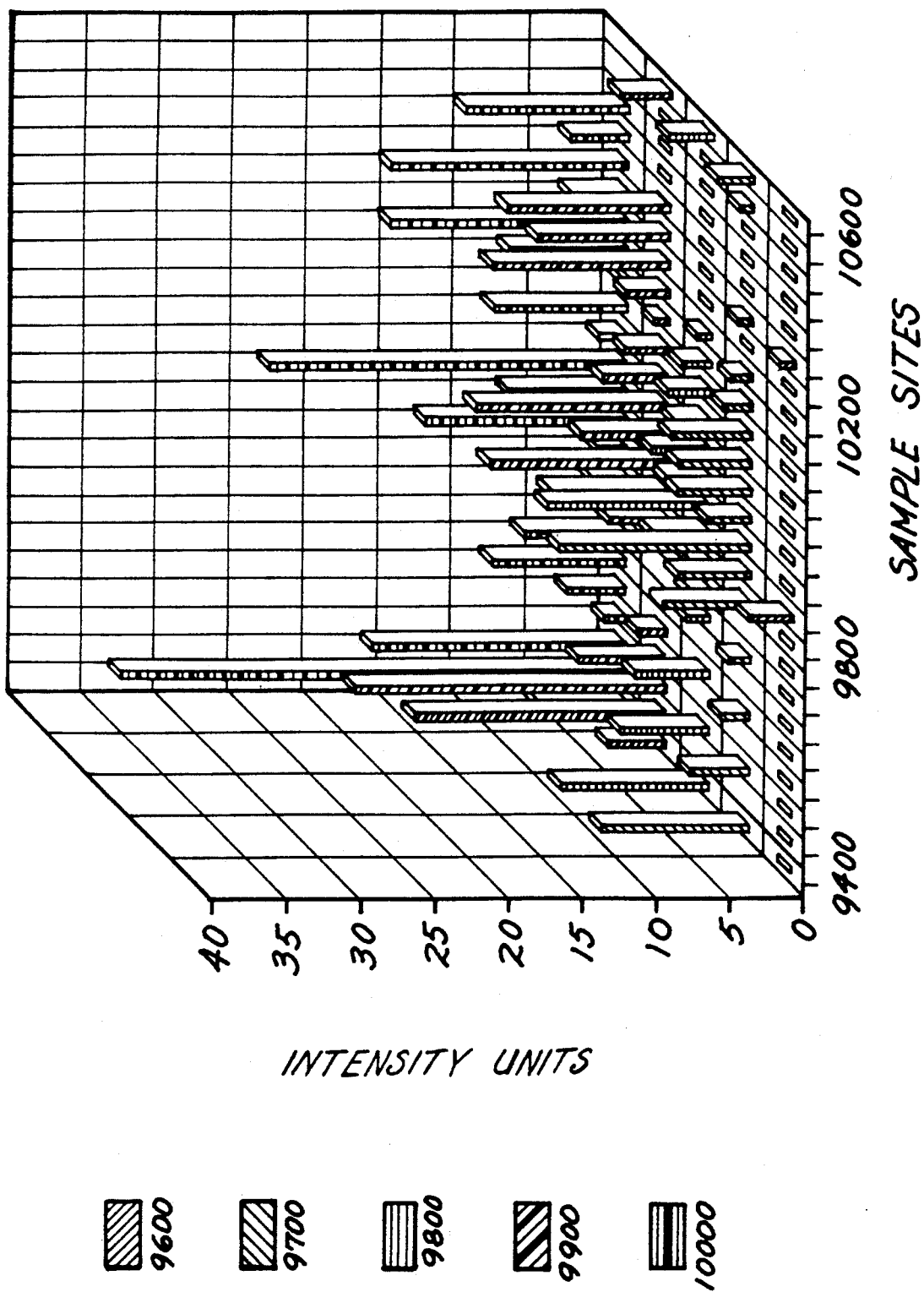
FIG. 3 is a three-dimensional plot illustrating how the detected binding of unimmunized rabbit serum (Intensity Units) is correlated with the geographical region (Sample Sites) from which the soil samples were obtained to indicate the location of underlying petroleum oil deposits; and, FIG. 4 shows similar data for a representative point pollution source.
Figure 4:
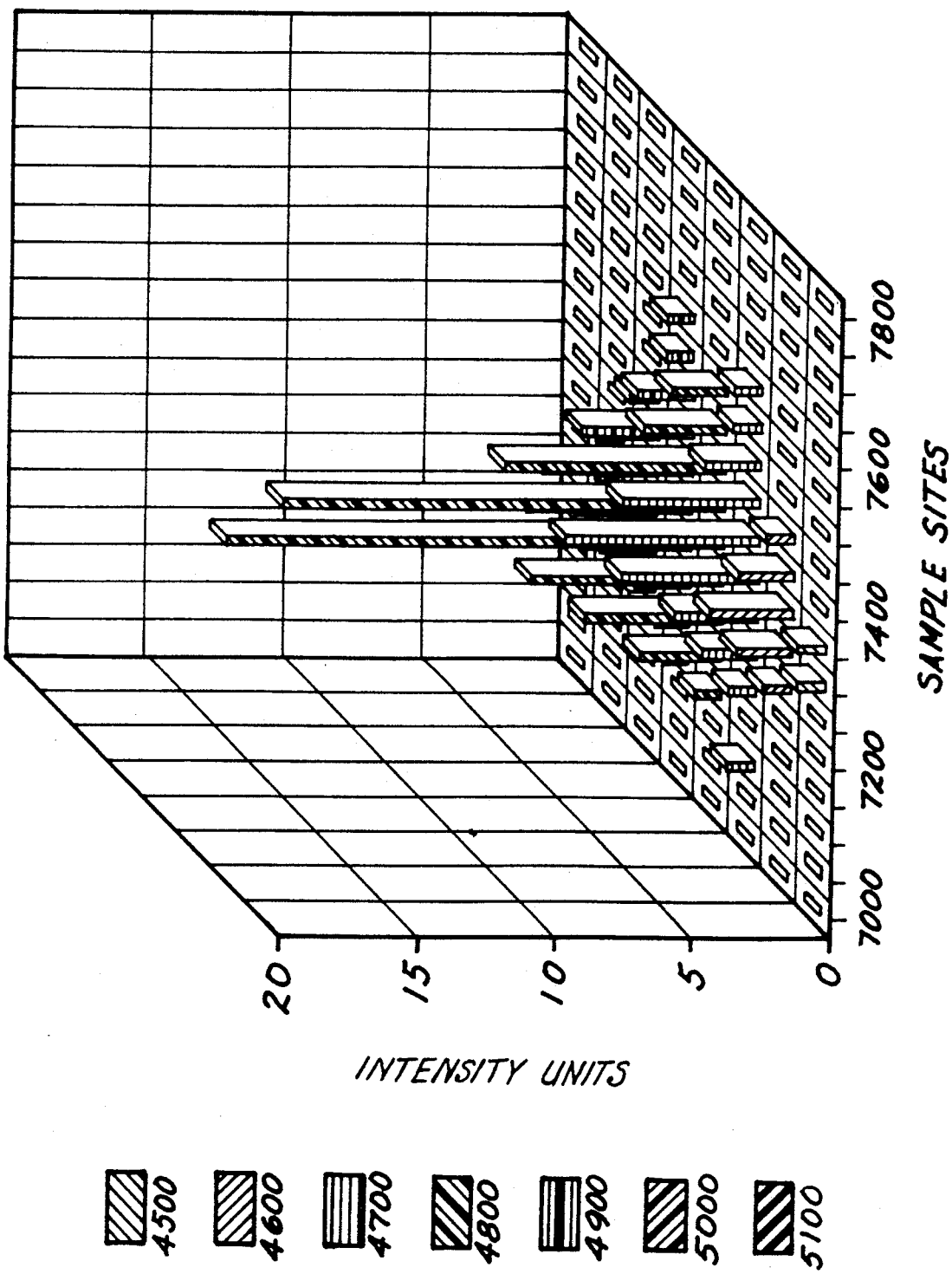

The present invention provides, in a representative embodiment, methods and kits for determining the presence of petroleum oils in soil samples. The invention is predicated upon the serendipitous discovery that petroleum oils from soil samples bind immunoglobulin molecules from the globulin fraction of rabbit serum, and that this immunologically nonspecific binding can be conveniently detected using available amplification techniques to provide a quick and economical method of oil exploration. In a more general sense, the invention enables analysis of samples for petroleum oils and other organic chemicals based upon immunologically nonspecific binding between a binding partner and a target analyte. Typically, the procedure and implementing kit can be used for determining the presence of hydrophobic hydrocarbons, e.g., long-chain alkanes. Preliminary investigations indicate that the technology can be used by the oil and gas exploration industry as a prospecting tool. The method and kit may also have a monitoring application in the environmental industry for the detection of toxic organic chemicals.

Immunologically Nonspecific Binding Partners

The invention provides an immunological indicator of protein(s) bound to or associated with hydrocarbons of interest. The prototype system uses rabbit serum as the protein solution to saturate the binding sites of the hydrocarbons. Rabbit serum is a complex heterogeneous solution composed of a variety of components, some of which include vitamins, minerals, sugars, salts, lipids, carbohydrates, and protein molecules. Immunoglobulins, which comprise a portion of the protein molecules in the serum, may be used as an indicator of hydrocarbons in the samples.

In a representative embodiment, the amount of rabbit immunoglobulin bound to the hydrocarbon is determined using an anti-rabbit immunoglobulin linked to a reporter molecule (e.g., goat anti-rabbit alkaline phosphatase IgG) for detection. The reporter molecule could alternatively be another enzyme, such as horseradish peroxidase or $\beta$-galactosidase; a radiolabel, such as $I^{125}$; a chromogenic or fluorogenic compound, such as rhodamine or fluorescein isothiocyanate (FITC), respectively; or part of a complex, such as avidin-biotin. The procedure can be used to determine the presence of hydrophobic hydrocarbons, e.g., long-chain alkanes in soil, sediment, and water samples.

The invention is not limited in terms of the particular binding partners that can be utilized as long as binding to the target analyte takes place under test conditions. In addition to immunological binding partners, e.g., from immunized and/or nonimmunized rabbits, other protein binding partners useful in the practice of the present invention are: proteins (e.g., avidin), domains of proteins capable of nonspecific interaction with an analyte (described below), etc. "Proteinaceous" refers to natural and synthetically modified proteins and protein domains.

Rabbit antibody is not the only component in the serum that could be used as the hydrocarbon binding partner. Other proteins or components of the serum (e.g., lipids, carbohydrates) could have the same or similar hydrocarbon binding characteristics and could be used as alternative binding partners. For example, albumin bound to a complex oil-based hydrocarbon could be detected using a secondary antibody raised against albumin and coupled to an enzyme amplification detection system (e.g., alkaline phosphatase and horseradish peroxidase) and could then be used to determine the amount of hydrocarbon-bound albumin.

In a preferred embodiment, the immunologically nonspecific binding partner is an immunoglobulin fraction obtained from a rabbit that has not been specifically immunized with an antigen. Immunoglobulins (Ig) or antibodies are proteins that offer humoral protection against viruses and bacterial pathogens in animals and humans. Immunoglobulins are a family of serum proteins with antibody activity which are remarkably heterogeneous but which have a number of common properties. The gamma globulin fraction of serum is rich in antibody activity, but other globulin fractions also contain antibodies. Antibodies from any of the known fractions of immunoglobulins can be used for the purposes of the present invention, as long as they are capable of immunologically nonspecific binding or associating with the target analyte.

In order to determine whether a given protein material is capable of binding or associating with a target analyte (e.g., a petroleum oil constituent such as a hydrocarbon, or other organic chemical), a controlled experiment analogous to the examples provided hereinbelow can be undertaken. Briefly, a putative protein binding partner can be contacted with several (e.g., 3-7) control samples containing known quantities of a target analyte, and contacted with a sample not containing any analyte, followed by detection of bound binding partner. If the amount of bound binding partner increases as a function of the amount of target analyte, then that particular binding partner may be useful for determining the presence of that target analyte. Generally, the binding is considered to be immunologically nonspecific as long as the target analyte was not used to produce an immunological binding partner specific to that analyte.

Target Analytes

The target analytes for purposes of the invention include petroleum oils and organic chemicals, especially toxic organic chemicals. The petroleum oils are typically associated with petroleum deposits, especially hydrocarbons. As used herein, the term "petroleum oils" includes natural gas, oil, and other organic chemicals typically used for commercial energy production. Such materials are generally predominantly hydrophobic hydrocarbons, e.g., long-chain alkanes (e.g., those having from 8-100 carbon atoms). The petroleum oils may also include compounds containing oxygen, sulfur, nitrogen, halogens, phosphorus, etc., depending upon the source.

The target analyte may alternatively be a toxic organic chemical capable of interacting with a binding partner in an immunologically nonspecific manner, in which case the invention provides methods and kits for detecting contamination of a site by the toxic organic chemical. As with the petroleum constituents, the binding partner binds to the target analyte (the organic chemical). The organic chemical may be a pesticide, dioxins, polychlorinated biphenyls, etc.

Samples

The samples may be any material suspected of containing a petroleum hydrocarbon or other organic chemical capable of an interaction with an immunologically nonspecific binding partner, as described herein. Typically, such samples will be soil, sediment, or water. The samples will usually be obtained from a geographical site (including land and/or water) suspected of containing deposits of petroleum oils or suspected of being contaminated by an organic chemical, usually a toxic substance.

Assay Procedure

The testing procedure involves contacting a sample with the immunologically nonspecific binding partner and then detecting the presence of any complexes of bound target analyte and binding partner. Conventional immunoassay protocols that involve immunologically specific binding may be applied analogously for detecting the binding partner in the present assay as long as the method does not substantially interfere with the nonimmunogenic interactions.

General Assay Procedure

Samples of soil, sediment, or water can be used as starting material. Soil or sediment samples should be air-dried immediately upon acquisition or at a minimum within two weeks of collection. Further delay will result in a reduction in the hydrocarbon content of the sediment or soil from biological activity.

Water samples should be frozen immediately upon acquisition. When required for use, the water samples should be thawed rapidly in a warm water bath (e.g., about 50° C.) to avoid degradation from bacteria that may be present.

A small amount of the sediment or soil is then added dispersed in a small volume of sterile water. The water containing the soil is then shaken vigorously for a short period of time. An aliquot of the soil-water mixture is then placed in one of the wells of a conventional microtiter plate. The material is then air-dried. The excess material is then washed from the plate. Next, a small amount of the enzyme-linked secondary antibody is added to the well, and the plates are allowed to incubate for a short period of time, allowing the secondary antibody to attach to the binding partner that has previously attached to any target analyte in the plastic well. Petroleum-based hydrocarbons will behave as a solvent when exposed to the plastic in the well. Therefore, since "like" dissolves "like", the hydrocarbon will be tightly bound to the plastic wall of the well. The excess, unbound secondary antibody is then washed from the plate with a buffer solution. The appropriate substrate is then added to the well. The plate is then left undisturbed for a period of time. The amount of substrate development is dependent on the amount of secondary antibody bound to the binding partner, and on the amount of time the plates are allowed for incubation. For soils, sediments, or water containing very small amounts of organic material, the period of incubation can be extended to increase the sensitivity of the analysis. The amount of substrate formed can then be determined with an available automatic or manual ELISA reader.

Data from a suitable number of samples is then plotted to represent the geographic hydrocarbon distribution.

For detection of binding, the immunologically nonspecific binding partner may be directly labeled with a compound or composition capable of providing a detectable signal, such as a fluorophore or radioisotope. Generally, since at most the amount of targeted analyte present in a sample will be a trace quantity, the means for detecting the binding partner bound to the analyte should, preferably, provide for amplification of the signal. Enzymes are particularly useful as labels, since they provide such amplification, in that a single active enzyme can act on a plurality of substrate molecules over a short period of time. Further, the conjugation of enzymes to proteins such as antibodies is well known and has received ample illustration in the literature. In addition, techniques for measuring enzymes providing spectrophotometric signals are well established. A wide variety of suitable enzymes are commercially available and have been extensively characterized. Examples of such enzymes are alkaline phosphatase and horseradish peroxidase. Any other enzyme that does not interfere with the immunologically nonspecific binding of the binding partner to the target analyte and that produces a detectable product can be utilized.

Various fluorescent labels may be employed, such as umbelliferone, fluoresceins, rhodamines, and naphthylamino compounds, e.g., 1-dimethylaminonaphthyl-5-sulfonate (Dansyl). The fluorescers which are employed will normally absorb light at wavelengths in excess of 300 nm, usually in excess of 350 nm, and preferably in excess of 400 nm. These fluorescers may be readily conjugated to protein by a variety of methods, such as disclosed in U.S. Pat. No. 3,996,345.

Various chemiluminescent substances may also be employed as labels, such as the 1,4-phthalazinediones, e.g., luminol(5-amino-2,3-dihydro-1,4-phthalazinedione), 6,7,8-trimethoxyluminol, and 9-dimethylamino benzo[H]-1,4-phthalazinedione; lophine, lucigenin, N-methyl 9-acylacridinum halides, luciferins, and the like. See McCapra, *Quarterly Reviews* 20:485, 1966.

Chemiluminescence can be measured with a photometer or a scintillation counter.

Illustrative reactants include: luciferin, oxygen, and luciferase; luciferin, hydrogen peroxide, and luciferase; luminol, hydrogen peroxide, and horseradish peroxidase; and, luminol and hydrogen peroxide.

Stable free radicals for use as labels include nitroxides, verdazyls, nitronyl nitroxides, and the like. For a general discussion of stable free radicals see Forrester, *Organic Chemistry of Stable Free Radicals*, Academic Press, New York, 1968.

Compounds which absorb light in the ultraviolet or visible region can be employed as labels, normally having absorption maxima greater than 300Å, more usually greater than 350Å, preferably greater than 400Å. A large number of dyes can undergo a change in their absorption spectra upon binding to a receptor; others can be readily reduced or oxidized to go from a colorless form to a colored form. Illustrative dyes include safranin, 2,6-dichlorophenol-indophenol, methylene blue, brilliant cresyl blue, phenazine methosulfate, Meldola blue, and the like. For the most part, only concentrations down to about $10^{-6}$M are detectable, so that light absorptive compounds would only be useful where relatively high concentrations of analyte are encountered.

Various reductants and oxidants can be employed which may be dyes (as described previously) or may provide a product which reacts with a dye. Of particular interest is where the redox reaction involves three materials which can be involved in cycling, where two of the materials cannot react or react only slowly without the intermediacy of the other material. For example, NADH, NADPH, and other dihydro-1,4 pyridines, e.g., Hanztsch ester, can be employed to reduce quinonediimines, e.g., Meldola blue and phenazine methosulfate, which will then react with a dye such as thiazolium blue.

The use of geochemical analytical procedures has become important in oil exploration (Philp, R. P., *Chemistry and Engineering Special Report*, Geochemistry in the search for oil, pp. 28–43, 10 Feb. 1986). A significant database has been established for the use of biomarkers (degradation products of petroleum oil components by microorganisms) for oil exploration. The use of these biomarkers complementsseismic and stratographic studies (Philp, 1986).

Furthermore, geochemical techniques will be instrumental in providing information on the "source, maturity, relative migration distances and the extent of biodegradation" of the petroleum (Philp, 1986). The immunogeochemical techniques discussed here will also make a significant contribution to the development of routine procedures. This is further enhanced by the potential of the technology discussed in this embodiment to detect the biomarkers in the petroleum-containing samples directly.

It is also possible not to label the binding partner itself, but to carry out a sandwich assay in which the initially bound (first) binding partner is caused to interact with a second binding partner that specifically binds with the first binding partner. The second binding partner should be labeled to provide detection of its presence, which in turn provides for detection of the first binding partner and hence the target analyte.

Kits

In performing assays it is a matter of substantial convenience, as well as providing significant enhancement in accuracy, to provide the reagents combined in a kit.

In providing a kit, the materials are offered as dry powders, lyophilized as necessary, or as concentrated solutions or as diluted ready-to-use solutions. The reagents are reconstituted or diluted to a specific volume, if required, which allows for accurate transfer and a predetermined final concentration and ratio of reagents.

Besides the reagents necessary for the assay, there will normally be other additives. Buffer will normally be provided as an adjunct reagent, although buffers may be included with one or more of the active reagents. Various stabilizers and preservatives may be included. Illustrative of such materials are proteins, such as serum albumin, gelatin, and egg albumen; polyols, such as glycerol and mono- and polysaccharides, e.g., guar gum and mannose; surfactants; preservatives, such as EDTA, sodium azide, and the like. The amount of protein employed will be sufficient to provide a final concentration in the reagent solution of from about 0.05 to 10 mg/ml. The glycerol may be used in amounts of up to 40% by weight. The other reagents will generally vary widely in amounts to provide from about 0.01 to 2000 $\mu$g/ml of reagent solution.

In one preferred embodiment, the invention provides a geochemical prospecting kit containing an enzyme-linked secondary antibody that will enable indirect, nonspecific but quantitative detection of trace amounts of petroleum constituents, or synthetic chemicals, e.g., pesticides, dioxins, and PCBs.

The invention now being generally described, the same will be better understood by reference to the following examples, which are included herein for purposes of illustration only, and are not intended to be limiting of the present invention, except where so indicated.

EXAMPLE 1

Discussion of Binding and Reaction of Rabbit Sera to Hydrocarbons With Subsequent Detection Using Anti-Rabbit Enzyme-Linked Immunoglobulins It is possible to immunize rabbits against the spores of *Bacillus cereus* (a common soil bacteria). When soil samples from mining regions are analyzed with immunized and unimmunized sera, a significant difference in immunoreactivity between the two analytical procedures is observed (FIG. 1). The magnitude of the difference between the immunized and unimmunized sera is directly related to the number of spores in the soil. When soils containing petroleum oil are similarly analyzed (FIG. 2), there is no observed difference between the sample analyzed with the immunized and unimmunized sera (FIG. 2). This relationship has been defined as the reaction of an immunologically nonspecific binding partner (rabbit serum) binding to an analyte (petroleum oil). The magnitude of the reaction with either the immunized or unimmunized serum appears to be directly related to the concentration of petroleum oil in the soil sample.

The correlation between rabbit serum and hydrocarbon content is based on the following observation. An immunologically nonspecific binding partner will bind to petroleum-based hydrocarbons (from soil, sediment and water samples), after the hydrocarbons have been bound to the plastic in the wells of microtiter plates (typically used for conventional ELISA assays).

In this embodiment, the amount of rabbit serum antibody bound is a function of the concentration of hydrocarbon present on the plastic wall of the microtiter well and, therefore, the sample. The advantage of this approach, unavailable in traditional geochemical analyses, is the inherent increase in sensitivity which the enzymatic detection system offers. This is especially true when considering the small sample size (e.g., 1 g of soil or sediment) that is required to perform the subject assay. Typical geochemical assays require in excess of 25 g of sample. In addition, the method is relatively simple and could be performed by personnel with a minimal amount of training, on site, and at relatively little cost.

Rabbit serum is not the only reagent that can be used for binding to complex hydrocarbons. Serum from other animals could be substituted. However, the relationship between the detection of complex petroleum-based hydrocarbons and rabbit serum appears to be species-specific. Calf serum, a major component of the "blocking solution," does not appear to react to petroleum in the soil and sediment samples, whereas the rabbit serum does.

The calf serum can be used, in this embodiment, to reduce the natural background associated with the analysis of soil samples of petroleum content. This also suggests that the relationship between the immunologically nonspecific binding partner and the organic analyte is specific to the animal species from which the serum has been obtained.

Therefore, specificity can be built into the analytical procedure with a careful selection of the serum and, therefore, the immunologically nonspecific binding partner.

EXAMPLE 2

A Representative Assay Procedure

One gram $\pm 0.1$ g of soil, free from twigs, needles, and stones, is placed in a sterile 18 mm glass test tube. Three milliliters of sterile deionized water (sd$H_2O$) is used to suspend the soil with three 5-second blasts on a vortex-mixer. The slurry is poured into one-half of a sterile petri plate. From there, 100 $\mu$l is conveniently transferred using a pipette into the wells of a Costar TM EIA 3590 plate. The volume of water used allows for adequate hydration of the soil, dislodging of the organic compound from the soil matrix, ease in transfer to the plate, and keeps the organic compound (the analyte) at a maximum concentration. Pipetting is made easier by cutting 5 mm from the tip of the disposable pipette tip.

The EIA plate with its twelve columns of eight wells allows for ten different soil samples and two controls. Each soil sample is placed in one set of the eight vertical wells, 100 $\mu$l per well.

100 $\mu$l of spore suspensions with different spore concentrations, i.e., $10^7$ to $10^{10}$, are added to the control wells in sequential order. Preparation of the spores and their dilution in sd$H_2O$ is discussed below. Once the soil samples and the control spore dilutions have been spotted on the EIA plate the samples are dried onto the plate by incubation at 37° C. overnight. The spore samples can be replaced with any control antigenic-based system. The system described here is convenient because the spores are both easy to prepare and, once prepared, are stable over a wide range of conditions.

The spores could be stabilized with a treatment of 4% formalin for 24 h.

The soil is removed after a 24-h incubation by either dipping the plate into TBS-T20 (Table 1) and flicking the wash and soil out, or using a squeeze bottle to rinse the material out. The selected procedure has to be sufficiently vigorous to remove all dirt particles. The dirt tends to attract charged particles, particularly antibodies or protein being used to assay the concentration of hydrocarbons in the sample. The wells are filled with the wash solution, left to stand for 5 to 10 minutes, and emptied. The routine is repeated 3 to 5 times until few particles remain. After expelling for the last time, the wells are filled with 100 μl of a blocking solution (calf serum; Table 2) and then incubated for a minimum of one hour at 37° C.

TABLE 1

TBS-T20(Tris-Cl Buffeed Saline with Tween 20)

50 mM Tris-Cl pH 7.6
0.85% NaCl
0.1% Tween 20

TABLE 2

Blocking Solution

10% Calf Serum
10% Glycerol
1M D-Glucose
TBS-T20

After incubation, the blocking solution is flicked out and the appropriate binding partner is applied. Serum from rabbits is currently being used to assay the concentration of organic material in the soil samples. The serum is diluted 1:1000 with the blocking solution. The immunized rabbit serum (100 μl) is deposited in each of the wells containing soil samples and in one set of eight wells containing the spore dilutions. 100 μl of the control serum (rabbit serum exposed to formalin treated $B.$ $cereus$ $spores$) is applied to one set of spore wells. In this way, variation in our analyses can be checked, and obvious erroneous results may be removed. The economic nature of the procedure has allowed extensive replication (8 to 10 replicates per sample). However, current investigations suggest that the intersample variation is small (less than 5%), and 2 to 3 replicates is probably sufficient, further enhancing the cost-effectiveness of the assay. After application of the serum the plates are incubated for one hour at 37° C.

The rabbit serum is removed by washing with TBS-T20 using the same procedure as removal of the soil particles. A specific antibody is then used to detect the primary binding partner. The antibody is goat anti-rabbit conjugated to alkaline phosphatase and is commercially available from many sources. The antibody is diluted to its "working dilution" as specified by the manufacturer with blocking solution. The solution (50 μl) is applied to each well, and the plate is incubated at 37° C. for one hour.

After incubation the conjugated antibody is removed by again washing with TBS-T20 following the procedure outlined in the initial plate wash. The substrate for the alkaline phosphatase is then applied to each well. The substrate, p-nitrophenylphosphate, is also commercially available and arrives in an easy-to-use tablet form. One tablet dissolved in 10% diethanolamine (Table 3) is enough substrate for one plate.

TABLE 3

| 10% Diethanolamine Solution |
| --- |
| 10 mls diethanolamine |
| 90 mls of $sdH_2O$ |
| 1 mM $MgCl_2$ |
| 0.02% Sodium azide |

One table is dissolved in 5 mls of 10% diethanolamine, and 50 μl of that solution is applied to each well. The plate is left to develop overnight and the optical density readings of the color development is read using commercially available automatic or manual ELISA readers.

The ELISA reader provides the results in the form of optical densities. The replicates are averaged. These values are plotted and compared. The value of the data to the exploration geologist is in the pattern or clustering of high and low values. Repetitively high values are indicative of the presence of hydrocarbon in the sediment, soil, or water sample.

Spore Preparation

Large spore preparations for use as antigen to immunize rabbits and to use as controls on the ELISA-plate were carried out in 2-liter flasks. Sterile G medium (500 ml; Table 4) was inoculated from a 10-ml overnight culture of a single lecithinase-positive colony isolated on an Egg Yolk Agar (EYA; described below) plate. The inoculum for the plate was a culture of *Bacillus cereus* isolated from soil. The progress of sporulation was monitored by performing the Shaeffer-Fulton (Table 5) spore stain on a small sample. When fewer than 1% of the bacteria is left in the vegetative state, the spores are centrifuged at 5000 rpm for 10 min., washed several times with $sdH_2O$, suspended in 10 ml of $sdH_2O$, and frozen at −20° C. in 1-ml aliquots. The concentration of the spore preparation is determined by serially diluting the preparation and spreading a 1-ml aliquot of the appropriate dilution on an EYA plate. The spores are then further stabilized with treatment with 4% formalin for 24 h.

TABLE 4

| G Medium | | |
| --- | --- | --- |
| Per liter: | 0.5 mg $FeSO_4.7H_2O$ | |
| | 10 mg $CuSO_4.5H_2O$ | |
| | 10 mg $ZnSO_4.7H_2O$ | |
| | 50 mg $MnSO_4.H_2O$ | |
| | 10 mg $CaCl_2.2H_2O$ | |
| | 0.8 g $MgSO_4.7H_2O$ | |
| | 1.0 g $K_2HPO_4$ | |
| | 2.0 g Yeast Extract | |
| | 4.0 g D-Glucose | |
| | 5.0 g $(NH_4)_2SO_4$ | pH 7.2 |

TABLE 5

| Schaeffer and Fulton Spore Stain | |
| --- | --- |
| a. | A smear is prepared from the culture, dried and fixed on a microscope slide. |
| b. | The smear is covered with an aqueous 5% malachite green solution for 30-60 seconds, then heated until it steams for 30 seconds. |
| c. | The slide is washed with tap water. |
| d. | The smear is then covered with safranin for 30 seconds. |
| e. | The slide is then rinsed with tap water, blotted, and air-dried. |

The spores stain green; the remainder of the cell stains red.

Yolk Agar Technique

EYA (after the method of Waterson, J. R., *Journal of Geochemical Exploration*, 23:243-252, 1985; Table 6) is an indicative medium that identifies the lecithinase-positive bacteria. Coupled with a pasteurization step, the EYA technique enables the enumeration of germinable spores of lecithinase-positive bacteria.

Appropriate dilution of the soil or spore samples, in this case $10^{-3}$ or $10^{-4}$, are made with $sdH_2O$. Care in mixing and pipetting must be taken, as a representative aliquot must be transferred to each successive dilution to obtain an accurate count. Once diluted, the solutions are placed in a 90° C. water bath for one minute and then quickly cooled in ice water. A 1.0-ml aliquot is transferred to an empty petri plate. Approximately 10 ml of EYA at 55° C. (still liquid) is poured into the plate and mixed well with the soil dilution. The agar is then allowed to solidify, the plate inverted, and placed at 30° C. for overnight incubation.

Lecithinase-positive colonies of *Bacillus cereus* appear gray-white on the agar, with a white opaque halo around the colony.

TABLE 6

| Egg Yolk Agar | |
|---|---|
| Per liter | 1.0 g $K_2HPO_4$ |
| | 0.2 g $MgSO_4.7H_2O$ |
| | 0.01 g $FeSO_4.7H_2O$ |
| | 0.01 g $CaCl_2.2H_2O$ |
| | 1.0 g D-Glucose |
| | 1.0 g $NH_4Cl$ |
| | 0.1 g Yeast Extract |
| | 8.0 g Agar |
| | $dH_2O$ to volume |

The solution is heated to aid dissolving, and pH adjusted to 7.2.

The solution is divided into 200-ml aliquots for easy handling, autoclaved, then cooled to 55° C.

To each 200-ml portion, 2.0 ml of sterile 50% trisodium citrate is added.

5 ml of egg yolk is next added to the 200-ml aliquots with stirring and while maintaining the 55° C. temperature.

EXAMPLE 3

Oil and Gas Exploration

Samples of soil or sediment material are collected using routine sampling procedures. The type of sample that this analysis can be used for includes: surface and near surface soil samples, sediment collected from land cores, sediment collected from marine and freshwater cores, and from interstitial fresh and marine waters.

After collection, the soil sample must be air-dried and then stored in a cool, dry climate. Samples that are kept in a "fresh" state for extended periods of time (greater than a few months) will be less useful for analysis. Improper storage of the samples will result in a reduction of the signal. It is currently not clear what causes the loss. Chemical changes and microbial degradation of chemicals in the sample probably contribute to the signal loss.

The samples are then analyzed according to the method described previously. Once the data has been collected, the data can then be plotted as shown in the representative FIG. 3. The geographic display can then be used to predict the location of underlying zones of hydrocarbon deposits.

EXAMPLE 4

Pollution Source Location

Samples of soil or sediment material are collected using routine sampling procedures. The type of sample that this analysis can be used for includes: surface and near-surface soil samples, sediment collected from land cores, sediment collected from marine and freshwater cores, and from interstitial fresh and marine waters.

As noted above, after collection, the soil sample must be air-dried and then stored in a cool, dry climate. Samples that are kept in a "fresh" state for extended periods of time (greater than a few months) will be less useful for analysis. Improper storage of the samples will result in a reduction in the signal. It is currently not clear what causes the loss. Chemical changes and microbial degradation of chemicals in the sample probably contribute to the signal loss.

The samples are then analyzed according to the method described above. Once the results have been collected, the data can be plotted as shown in the representative FIG. 4. The graph can then be used to pinpoint the location of the pollution problem.

While the present invention has been described in conjunction with preferred embodiments, one of ordinary skill after reading the foregoing specification will be able to effect various changes, substitutions of equivalents, and other alterations to the compositions and methods set forth herein. It is therefore intended that the protection granted by Letters Patent hereon be limited only by the definition contained in the appended claims and equivalents thereof.

The embodiments of the invention in which an exclusive property or privilege is claimed are defined as follows:

1. A geochemical method of exploring for petroleum oils, comprising:

contacting a soil sample from a geographical region with serum from a rabbit that has not been immunized with petroleum oils;

detecting binding of the rabbit serum to the sample; and correlating the detected binding to the presence of petroleum oils in the geographical region from which the soil sample was obtained.

* * * * *